United States Patent [19]
Chiang et al.

[11] Patent Number: 5,875,797
[45] Date of Patent: Mar. 2, 1999

[54] DENTAL FLOSS

[75] Inventors: Casper W. Chiang, Danville, Calif.;
Edward Hosung Park, Sharon, Mass.;
Brad Castillo, San Ramon, Calif.;
Mingchih Michael Tseng, Hingham, Mass.

[73] Assignee: Gillette Canada Inc., Kirkland, Canada

[21] Appl. No.: 743,722

[22] Filed: Nov. 6, 1996

Related U.S. Application Data

[63] Continuation-in-part of Ser. No. 699,890, Aug. 15, 1996, abandoned, which is a continuation-in-part of Ser. No. 467,814, Jun. 6, 1995, and Ser. No. 471,636, Jun. 6, 1995.

[51] Int. Cl.[6] ............................................. A61C 15/00
[52] U.S. Cl. .................... 132/321; 132/323; 132/329; 156/180; 264/172.11
[58] Field of Search ..................... 132/321, 323, 132/329, 309; 156/180, 167, 161, 305, 308.6, 309.6, 229, 244.11; 264/172.11, 172.12, 172.13, 172.14, 172.15, 176.1, 210.8; 428/399, 370, 373

[56] References Cited

U.S. PATENT DOCUMENTS

| | | |
|---|---|---|
| 3,699,979 | 10/1972 | Muhler et al. . |
| 3,761,348 | 9/1973 | Chamberlin ............................. 132/321 |
| 3,800,812 | 4/1974 | Jaffe . |
| 3,860,013 | 1/1975 | Czapor ...................................... 132/91 |
| 3,897,795 | 8/1975 | Engel ....................................... 132/321 |
| 4,215,478 | 8/1980 | Thomas et al. . |
| 4,424,258 | 1/1984 | Bach ........................................ 428/370 |
| 4,583,564 | 4/1986 | Finkelstein et al. ..................... 132/321 |
| 4,646,766 | 3/1987 | Stallard . |
| 4,911,927 | 3/1990 | Hill et al. . |
| 4,963,346 | 10/1990 | Amer . |
| 5,021,267 | 6/1991 | Gent et al. . |
| 5,051,401 | 9/1991 | Sikes . |
| 5,079,288 | 1/1992 | Humphries et al. . |
| 5,098,711 | 3/1992 | Hill et al. . |
| 5,300,290 | 4/1994 | Spencer . |
| 5,357,990 | 10/1994 | Suhonen et al. ......................... 132/321 |
| 5,372,885 | 12/1994 | Tabor et al. ............................. 428/373 |
| 5,479,952 | 1/1996 | Zachariades et al. ................... 132/321 |
| 5,508,334 | 4/1996 | Chen ........................................ 132/321 |

*Primary Examiner*—Gene Mancene
*Assistant Examiner*—Pedro Philogene
*Attorney, Agent, or Firm*—Fish & Richardson P.C.

[57] ABSTRACT

Improved dental flosses include two or more components selected to provide desired properties to the floss. The improved flosses may comprise one or a plurality of multi-component filaments, each filament including an inner core selected to provide strength to the floss, and an outer layer selected to provide a desired surface property. The improved flosses also may comprise one or a plurality of core filaments embedded in a single body sheath. The filament component provides desirable physical properties to the floss, such as tensile strength, while a floss body sheath component provides desirable surface properties.

39 Claims, 9 Drawing Sheets

 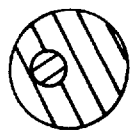 
FIG. 3.    FIG. 3a.    FIG. 3b.
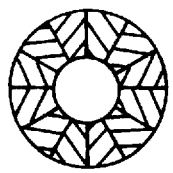 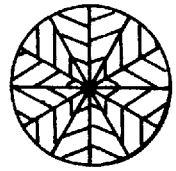
FIG. 3c.    FIG. 3d.
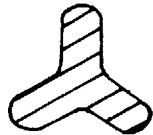 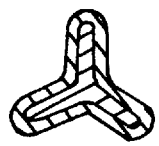
FIG. 4.    FIG. 4a.
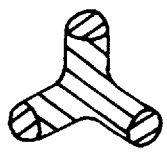
FIG. 4b.

DENTAL FLOSS

CROSS-REFERENCES

This application is a continuation-in-part of U.S. patent application Ser. No. 08/699,890, and filed on Aug. 15, 1996, now abandoned, which is a continuation-in-part of earlier-filed U.S. patent applications, Ser. Nos. 08/467,814 and 08/471,636, both filed on Jun. 6, 1995, now pending. We claim priority to all of these preceding applications under 35 U.S.C. § 120, all of which are incorporated herein by reference.

Applicants also hereby incorporate by reference U.S. Patent Application entitled "'Gel' Dental Floss," Ser. No. 08/699,891, filed concurrently herewith on Aug. 15, 1996.

FIELD OF THE INVENTION

This invention relates generally to the field of filaments and extrusion methodology for producing such and more particularly relates to multicomponent floss filament materials and methods for producing such.

BACKGROUND OF THE INVENTION

Tooth decay and dental disease can be caused by bacterial action resulting from the formation of plaque about the teeth and/or the entrapment of food particles in interstices between the teeth. Removal of plaque and entrapped food particles reduces the incidence of caries, gingivitis, and mouth odors as well as generally improving oral hygiene. Conventional brushing has been found to be inadequate for removing all entrapped food particles and plaque. To supplement brushing, dental flosses and tapes are used.

Dental flosses, both in brush and thin floss form, often include additives such as flavors or colors. These flavors have been conventionally applied by coating the additive onto the surface of the floss.

SUMMARY OF THE INVENTION

Improved dental flosses are formed of multiple filaments that include two or more components selected to provide desired properties to the floss. For example, the filaments may include an inner core selected to provide strength to the floss, and an outer layer selected to provide a desired surface property, e.g., slipperiness, softness, or abrasiveness, or to deliver/release a flavor, clinical, or other compound. Manufacturing floss from two or more different components can provide the floss with the desired characteristics of each component (e.g., good tensile strength and slipperiness), which otherwise might be unavailable from a single component.

Multicomponent dental flosses referred to as the "islands-in-the-sea" embodiment include one or more inner filament cores ("islands"), which provide for a high degree of structural integrity including desirable tensile strength, embedded in a single floss body/outer continuous sheath ("sea") which provides desirable surface properties to the floss, such as slipperiness, softness or a more abrasive surface. A separate sheath surrounding the floss body may also be used to provide desirable surface properties to the floss.

A further aspect of the invention features improved multicomponent dental flosses in which one or more of the components includes an additive, e.g., a color, fragrance, flavor or active ingredient, which is releasable from the floss. The additive-containing component(s) may be water-soluble, to allow the additive to leach from the floss during use, or the floss may release the additive upon bulking. The additive may be provided as supplied, in microencapsulated form, or adsorbed or absorbed onto another additive, e.g., a particulate filler. The additive can also be provided on charged microspheres, as described in U.S. Pat. No. 5,300,290, the disclosure of which is incorporated herein by reference.

Advantageously, additives can be incorporated into the flosses of the invention during manufacture of the filaments, rather than applying the additives later during separate coating steps. This not only reduces the number of processing steps, but also reduces the amount of additive needed.

The improved flosses of the invention can be made by a method which includes coextruding two or more polymers through a multicomponent die to form a plurality of multicomponent filaments; and treating the filaments to form a multifilament fiber adapted for use as a dental floss.

The method for manufacturing "islands-in-the-sea" includes coextruding two or more polymers through a multicomponent die-and-slot arrangement to form filaments of one or more components embedded in a body of another component. Specifically, one or more filaments, each having an inner core and an outer sheath of a different material, are simultaneously coextruded through a die with multiple, separate, small-diameter holes. These filaments are then immediately forced through a slot, causing the filament sheath material to coalesce into a continuous floss body in which the core filaments are embedded.

Additionally, the invention features methods of flossing the teeth of, e.g., a human, by inserting between two teeth a length of a dental floss of the invention, and also features flosses with a pearlescent appearance.

Other features and advantages of the invention will be apparent from the drawings, the following Detailed Description, and the claims.

BRIEF DESCRIPTION OF THE DRAWINGS

FIGS. 3–3d are cross-sectional views, taken radially, of multicomponent coextruded filaments having various cross-sections.

FIGS. 4–4b are cross-sectional views, taken radially, of a trilobal single component filament according to one embodiment of the invention, a trilobal multi-component filament having a sheath/core cross-section, and a trilobal multicomponent filament having a tipped cross-section, respectively.

DESCRIPTION OF THE PREFERRED EMBODIMENTS

Figure 1:
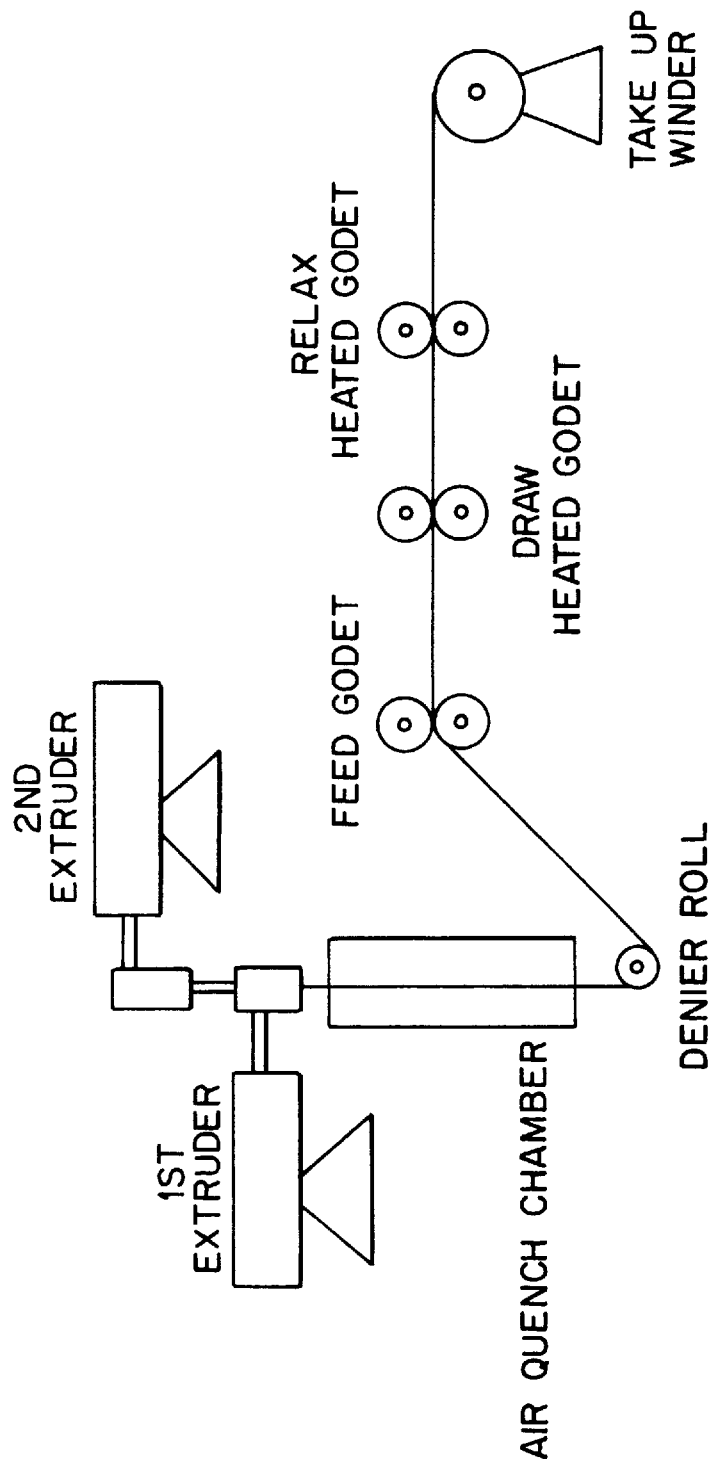
FIGS. 1 and 1a are schematic views of production lines for manufacturing coextruded dental floss according to the multifilament and the "islands-in-the-sea" embodiments of the invention, respectively.

Before the present multicomponent dental flosses and processes for extruding such are described, it is to be understood that the invention is not limited to the particular embodiments or extrusion methodologies described. Such floss components and methodologies may, of course, vary. It is also to be understood that the terminology used herein is for the purpose of describing particular embodiments only, and is not intended to be limiting. Instead, the scope of the present invention will be established only by the appended claims.

It must be noted that as used in this specification and the appended claims, the singular forms "a", "an" and "the" include plural reference unless the context clearly dictates otherwise. Thus, for example, reference to "a polymer" includes mixtures of different polymers.

Unless defined otherwise all technical and scientific terms used herein have the same meaning as commonly understood to one of ordinary skill in the art to which this invention belongs. Although any methods and materials similar or equivalent to those described herein can be used in the practice or testing of the present invention, the preferred methods and materials are now described. All publications mentioned herein are incorporated herein by reference.

DEFINITIONS

By "multicomponent," we mean that the filaments have two or more components, each comprised of a different material and preferably materials with different physical properties; by "coextruded", we mean that at least two of the components are present in the form of substantially separate phases having a distinct interface between them, rather than being intermixed after simultaneous but separate extrusion. The filaments are preferably formed by processes which are referred to in the art as "coextrusion", but the term "multicomponent coextruded", as used herein, encompasses filaments having the structure described herein which are manufactured by processes other than coextrusion. The term "dental floss", as used herein, is defined to include dental flosses, dental tapes, and similar articles.

PREFERRED EMBODIMENTS OF FLOSSES

In a first embodiment of the invention, the floss includes multiple, multicomponent filaments. Each of the multiple components of each filament contributes a desired physical property to the filaments and thus to the floss. Some preferred filaments include an outer sheath which is soft, slippery, or abrasive, to improve the ease of insertion, comfort and cleaning capability, respectively, of the floss, and an inner core that provides other desired physical properties such as higher tensile strength and resiliency than are available with the sheath material alone and/or serves as a carrier for additives, such as flavors, scents and medicaments. These filaments may or may not impart bulking capability to the floss, as disclosed in U.S. patent application Ser. Nos. 08/467,814 and 08/471,636.

Where the outer layer is intended to provide softness to ease insertion of the floss between the user's teeth, preferred polymers include TPEs (thermoplastic elastomers), e.g., poly (ether-amide) block copolymers, such as those available under the tradename PEBAX® from ELF Atochem, polyester elastomers such as those available under the tradename HYTREL® from DUPONT, and styrene-butylene block copolymers such as those available under the tradename KRATON® from Shell; EVA (ethylene vinyl acetate); ethylene-propylene copolymers; low MFI polypropylene, and mixtures thereof; and any other elastomer modified with compatibilizers (such as maleic anhydride, acrylic acid, and glacidal methylacrylate (GMA) ), all as known in the art. More specifically, the outer layer can be made of PEBAX 2533; modified PEBAX, such as PEBAX 2533 or PEBAX 3533 with between 1 and 10% (preferred 3%) fatty acid amide wax added to increase slipperiness; or PEBAX 2533 modified with 1 to 20 percent, and more preferably 2 to 10 percent, functionalized styrene-ethylene-butylene-styrene (SEBS) block copolymer (e.g., grafted KRATON) to improve softness. Hardness of the outer layer material may range from Shore A 00 to 80.

Where the outer layer is intended to provide slipperiness to ease insertion of the floss between the user's teeth, preferred polymers include polyethylene, melt-extrudable fluoropolymers (e.g. polyvinylidene fluoride (PVDF), and fluorinated ethylene propylene copolymers), polymers containing polytetrafluoroethylene (PTFE) particles and/or silicone oil, blends of copolymers of PVDF and PTFE, such as those available from 3M under the tradename THV®, melt-extrudable lubricating polymers (e.g., polyoxyethylene such as is commercially available from Union Carbide under the tradename Polyox®, or triblock copolymers of polyethylene oxide and polypropylene oxide such as those available from BASF under the tradename Pluronic®), and melt-extrudable lubricous polymer alloys (e.g., Lubriloy® polymers available from LNP engineering plastics). PEBAX with 10% PTFE particles may also be used.

If the outer layer is to include an abrasive, for improved cleaning, preferred abrasive/polymer combinations include nylon containing particles of kaolin, calcium carbonate, zinc oxide, silica, PTFE, or blends of these particles which are compatible. If desired, one or more additives may be absorbed or adsorbed on the surface of the abrasive particles, e.g., by drum drying, spray drying, fluidized bed processing, or other suitable methods as is known in the art.

In all of the above cases, one of the polymers is preferably a reinforcing polymer, e.g., nylon, polyester or polypropylene, to impart tensile strength and/or rigidity to the floss. Hardness of the reinforcing polymer may range from Shore D 15 to 80.

Preferred resulting flosses contain from 72 to 288 filaments, and have a total denier of from about 400 to about 3000. More preferable flosses include 144 filaments with a total denier of about 500 to about 1000. Filaments have a preferred tensile strength of between 3–6 grams per denier (gpd), and a breaking strength of between 2 and 5 kg, with a preferred minimum breaking strength of 2.5 kg.

The sheath-and-core arrangement of filaments according to the present invention may have any suitable cross-section, preferably a symmetric sheath/core cross-section (FIG. 3b) or an eccentric sheath/core cross-section (FIG. 3a). The filament may also have a hollow pie cross-section (FIG. 3c), and, if desired, the hollow core may be filled with an additive, e.g., a flavor, color or active ingredient. Alternatively, it may have a side-by-side arrangement (FIG. 3) or a pie cross-section. (FIG. 3d).

Alternatively, preferred flosses include a plurality of filaments having a "multilobal" cross-section, as shown in FIG. 4. Preferred filaments include from 3 to 8 "lobes"; one suitable filament has 3 "lobes," as shown in FIGS. 4–4b. The filaments are preferably formed by extrusion through a die having the appropriate "multilobal" cross-section.

These filaments may be multicomponent or single component, and, if the former, may have a sheath/core (FIG. 4a), tipped (FIG. 4b), or other suitable cross-section. Suitable polymers for use in forming multilobal filaments include but are not limited to polyester, polypropylene and nylon. In multicomponent filaments, if desired, the polymers may be selected to render the floss capable of bulking.

Figure 5:
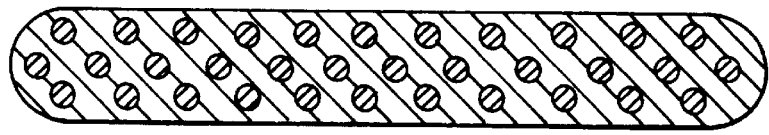
FIGS. 5–5e are cross-sectional views of various embodiments of a floss having filaments embedded in a floss body.
Figure 5A:
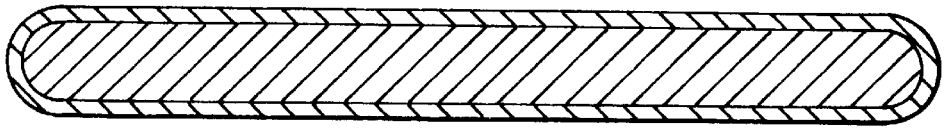
Figure 5B:
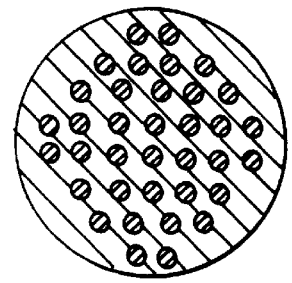
Figure 5C:
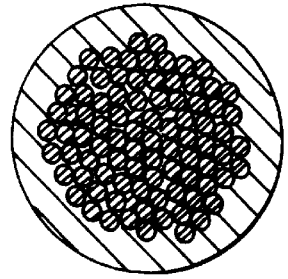

In another preferred embodiment of the invention, multiple single-component filaments are embedded in a coextruded second component, as shown in FIGS. 5, 5b and 5c. The second component forms the "sea"—the body of the floss—which surrounds the filament "islands."

As with the core material of the first preferred embodiment, the component material of the filaments provides desired physical properties such as higher tensile strength and resiliency than are available with the second component alone. The material of the body of the floss could provide a surface which is soft, slippery, or abrasive, to improve the ease of insertion, comfort and cleaning capability, respectively, of the floss. Either component could serve as a carrier for additives such as flavors, scents, or medicaments. Thus, each component of the floss contributes a desired property to the floss in the same manner as each component contributed a desired property to each filament of the floss in the first embodiment.

For this islands-in-the-sea embodiment, preferred core filaments include polyamides (e.g., nylon 6, or nylon 6—6), and have molecular weights between approximately 13,000 and approximately 25,000, with a tensile strength equal to or greater than approximately 4 grams per denier. The combination of nylon filaments embedded in a PEBAX® body provides acceptable properties for the floss. Examples of desirable properties include a hardness in the range of Shore D 15 to 50, a breaking tensile strength of approximately 2500 to approximately 8000 psi, and abrasion resistance in the approximate range of 70 to 94 mg/1000 cycles, using the Taber Abrasion Test (H18 wheel). Flosses in this embodiment also exhibit elongations at break in the range of 300 to 1500% of original length, and elasticities with a modulus on a stress/strain curve between 300 and 13000 psi.

In this preferred embodiment, FIGS. 5 and 5b show that the body component of the floss entirely surrounds each of the filaments. However, the floss could also be constructed as a number of filaments contacting other filaments to form a bundle, the bundle being coated with the second component that covers the bundle, as depicted in FIG. 5c.

Although many ratios of first to second components in the "islands-in-the-sea" embodiment are available, depending upon the desired characteristics of the floss, it is generally preferred that the floss cross-sectional area has greater than 50% of its area attributed to the first, strengthening component of the filaments, with a preferred ratio of cross-sectional areas of 30% floss body component: 70% filament component. A given ratio of body component:filament component can be achieved by varying the number of filaments and/or the cross-sectional areas of each filament. Further, the preferred ratio can be varied depending on the strength of the island material: the higher the tensile strength of each embedded filament, the lower the amount of filament material necessary to impart the desired tensile strength to the floss. By varying the pressure of each component as it passes through the spinneret (described below), one may vary the ultimate ratio of core component:sheath component. Any number of filaments is possible, provided that the floss "sea" is large enough to encompass all of them. From 1 to 49 filaments are preferred, more preferably about 30 to about 50 embedded filaments, with 34 filaments most preferred, arranged in three offset rows of 11, 12 and 11 filaments in a "sea" of another component. FIG. 5 shows an expanded view of floss with a roughly rectangular or flattened oval cross-section having thirty-four "island" filaments of a first component. The filaments are preferably offset, as shown in FIG. 5, rather than positioned directly above and below one another, to provide increased shred resistance. It has also been found that an arrangement of forty-six core filaments arranged in offset rows of 15, 16 and 15 filaments provides a floss with desirable characteristics. Preferred flosses have a total denier of from about 500 to about 1500.

Figure 5D:
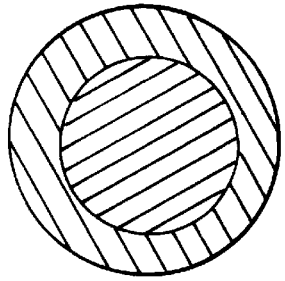

The degree of hardness of this embodiment can be increased by increasing the ratio of filament component to body component. The highest degree of hardness would be achieved with the embodiments shown in FIGS. 5a and 5d, which have a solid core made of the filament component, surrounded by a layer of the body component.

FIG. 5b shows an embodiment of circular cross-section In both FIGS. 5 and 5b, the second component creates the entire exterior surface of the floss. This uniform exterior surface permits this embodiment to better resist "shredding"—filament separation—sometimes experienced in the multiple multicomponent-filament embodiment during flossing.

Figure 5E:
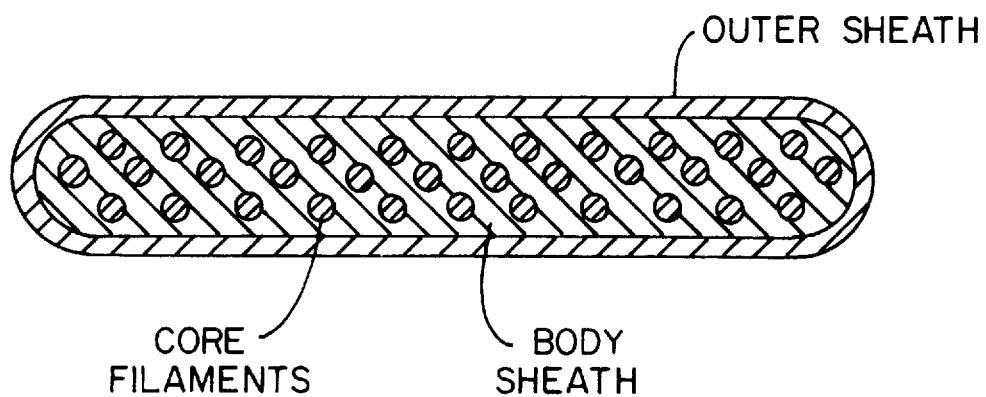

A variation on the "islands-in-the-sea" embodiment of the present invention is shown in FIG. 5e. This embodiment has an outer sheath surrounding the body sheath (or "sea" material) in which the core filaments are embedded. In the "islands-in-the-sea" embodiment, if too soft a material is used for the "sea," the floss may deform during processing and use, causing the user to lose the advantages of the present invention. The outer sheath material may be chosen to improve processing and use of the floss by having better handling characteristics than the "sea" material (by, for example, being harder), while simultaneously imparting desirable surface characteristics to the floss, such as high lubricity. Thus, this embodiment has the strengthening component of the core filaments, the component to provide softness to the floss in the "sea", and the lubricous component in the outer sheath. The outer sheath preferably comprises up to about 10% of the total floss cross-sectional area.

The described preferred embodiments can be formulated to include one or more additives, e.g., a color, fragrance, or active ingredient, in one or more of the components of the floss. One or more of the components may contain an additive such as chlorhexidine (or a salt thereof), sodium fluoride, flavor (e.g. Polyiff®, International Flavors and Fragrances), fragrance, tooth desensitizer, tooth whitener or other additives suitable for use in dental flosses. The thermoplastic to be used to carry the additive will be determined by the additive used, as would be readily appreciated by one skilled in the art. Suitable polymers for the core to carry additives include nylon, polyester, polypropylene, ethylene vinyl acetate (EVA), polyvinyl alcohol, polyethylene and alike. The inner or outer polymer may be water soluble to allow the additive to leach out of the polymer. Alternatively, for the multiple multicomponent-filament embodiment, the additive can be released upon bulking of the resulting floss.

The additive, if desired, can be incorporated in encapsulated form. Encapsulation may be used for thermal protection or moisture protection of the additive, and may be accomplished by any number of conventional techniques such as spray drying, drum drying or solvent evaporation. The additive can also be provided on a charged microsphere, as described in U.S. Pat. No. 5,300,290.

When a relatively transparent sheath material is used, the flosses may be colored with pigments to obtain a tinted or colored product. A preferred pigment is a pearlescent pigment. These pearlescent pigments may be added to the sheath (in a core/sheath configuration) or to the sea (in the islands/sea configuration). Optionally, a small amount of white pigment such as titanium dioxide (TiO$_2$) is added to opacify the clear sheath or sea.

Pearlescent pigments are often tinted red, blue, green or white. Preferred pearlescent pigments include coated micas, such as Mearlin from Mearl Corporation (Engelhard) or Hanna Color number 100001295 or 100001157 from M. A. Hanna. Particle sizes of these pigments are in the range of from about 1 to 15 microns (preferably from about 1 to 10 microns). These pigments are typically loaded in the core or sea layer at levels of from about 6 to 8% by weight. When titanium dioxide is used, its loading levels are from about 0.5 to 4%. Optionally, TiO$_2$ can be loaded in the core or islands at a level of from about 0.5 to 4% (preferably from about 2 to 4%). Pearlescent pigmented flosses have improved aesthetics and acceptable mechanical strength.

PREFERRED METHODS FOR MAKING PREFERRED EMBODIMENTS

A preferred method for forming a dental floss of the first embodiment of this invention is shown schematically in FIG. 1. First, two or more polymers are coextruded through a two-component coextrusion die. The polymers are chosen to produce a floss having the desired physical properties and/or the relative cross-sections, as described above.

Figure 2:
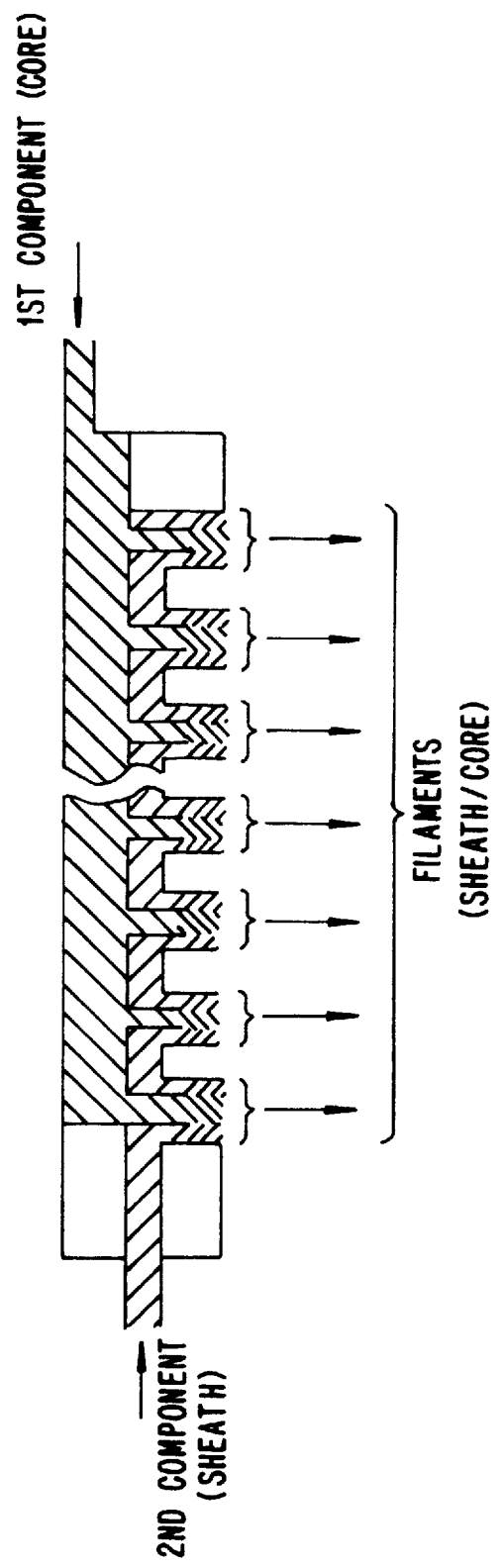
FIG. 2 is a cross-sectional view of a spinneret usable to produce multicomponent, coextruded flosses of the present invention.

Preferably, the coextrusion die includes a spinneret, as is known in the filament forming art. To produce a floss having multiple multicomponent filaments, both polymers are coextruded through spinneret having a plurality of small-diameter holes having the desired cross-sectional configuration. A spinneret suitable for producing multiple sheath-and-core filaments is shown in cross-section in FIG. 2. Multiple bicomponent filaments are coextruded simultaneously. The filaments exiting the spinneret are gathered together and pass through a cooling chamber with ambient temperature air flowing over the filaments at 60 to 120 cubic feet per minute to quench the polymer. The filament bundle is placed under high tension as it travels between two drawing godets which are rotating at different speeds. The tension applied to the fiber is expressed as the "drawdown ratio", which is the speed differential between the two drawing godets. As is known in the art, preferred drawdown ratios are from about 1.0 to about 5.0, more preferably about 1.5 to about 4.5, and most preferably about 3.5 to about 4.0. The fiber then passes through a relaxing godet and is collected on a take-up winder. For producing bicomponent flosses with multiple filaments, tension is generally preferably applied during manufacture, as this has been found to improve the tensile strength of the filaments. The art of drawing the filaments on heated rollers and different speeds and with different numbers of wraps per roller is part of standard polymer processing technology.

The resulting fiber can then be further treated to form a finished floss. For example, preferred flosses are twisted, preferably about 1 to about 3.5 twists per inch, most preferably about 2.5 twists per inch. Twisting reduces excessive filament separation and improves fray resistance. Twisting processes are well known, e.g., using standard ring twisting equipment. The resulting floss may also be coated in wax, as is known in the art.

Figure 6:
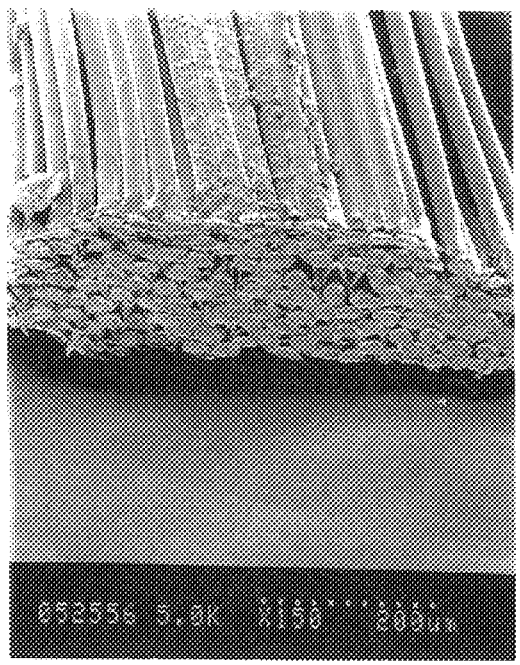
FIGS. 6–6a are electronmicrographs of a floss having multiple bicomponent, sheath-and-core filaments.
Figure 6A:
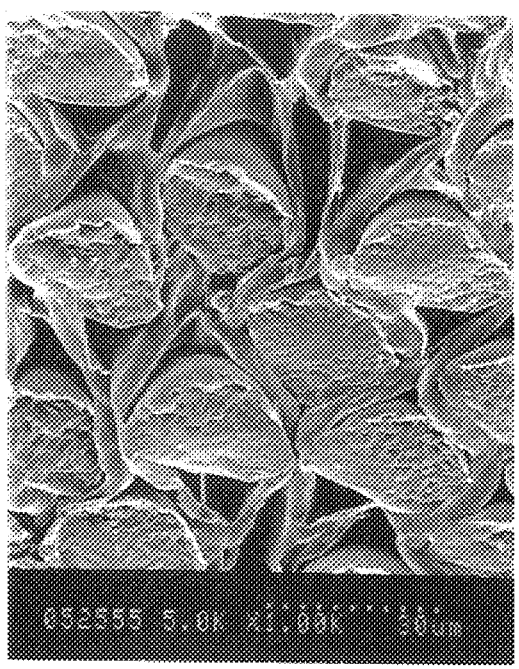

In one embodiment of the invention, one of the polymers may be selected to have a suitable melt temperature and other properties to enable the filaments to bond to each other to form the finished floss without the coating and twisting procedure described above. A suitable multicomponent fiber for use in this embodiment is described in Example 1. The filaments are bonded by softening and flattening the fiber on a heated draw roll as it is passed over the godets. Electron-micrographs of such a floss are shown in FIGS. 6 and 6a at 120× and 1000×magnification, respectively. The bonding of the sheath elastomeric material is clearly visible in FIG. 6a.

Figure 1A:
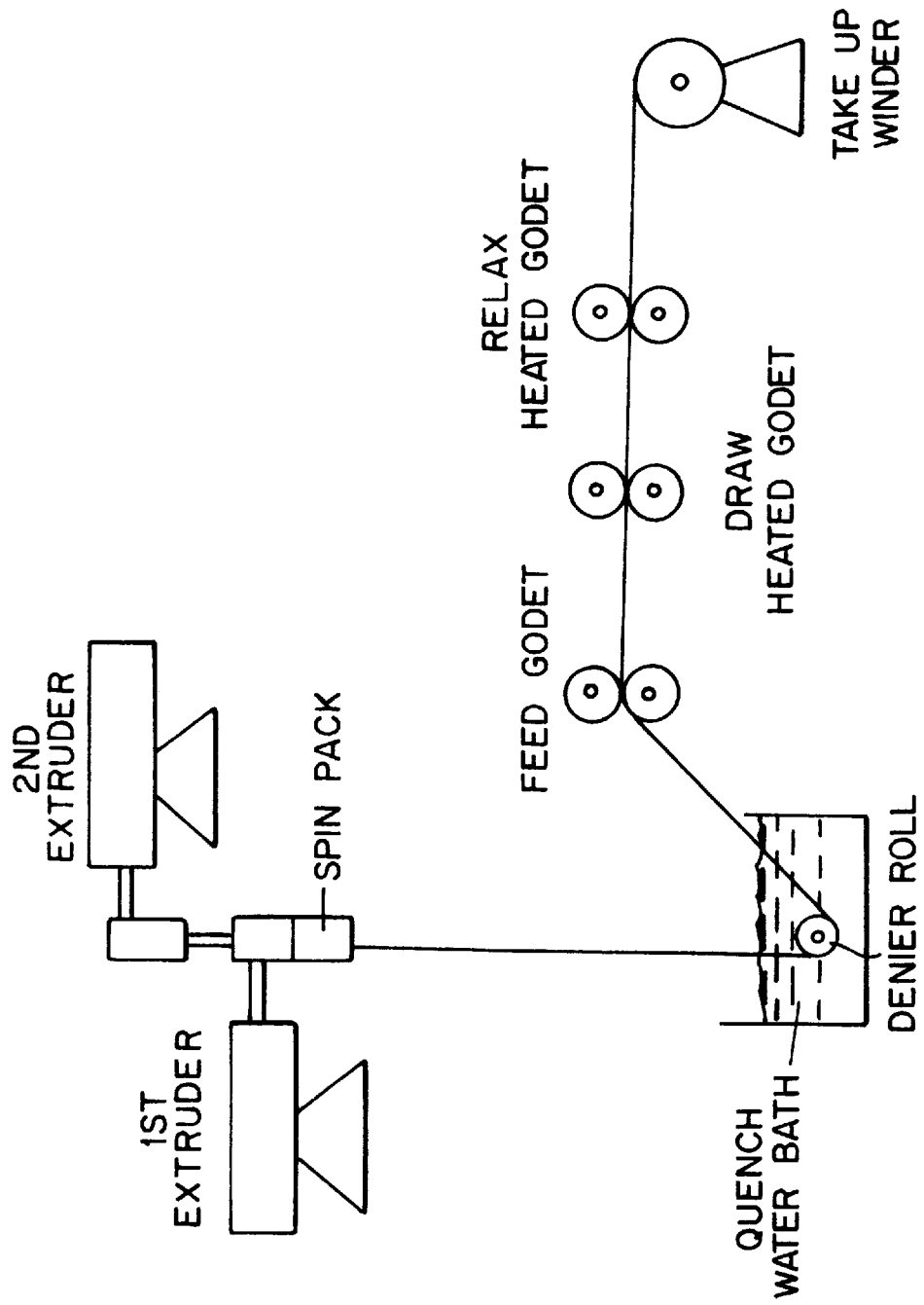
Figure 2A:
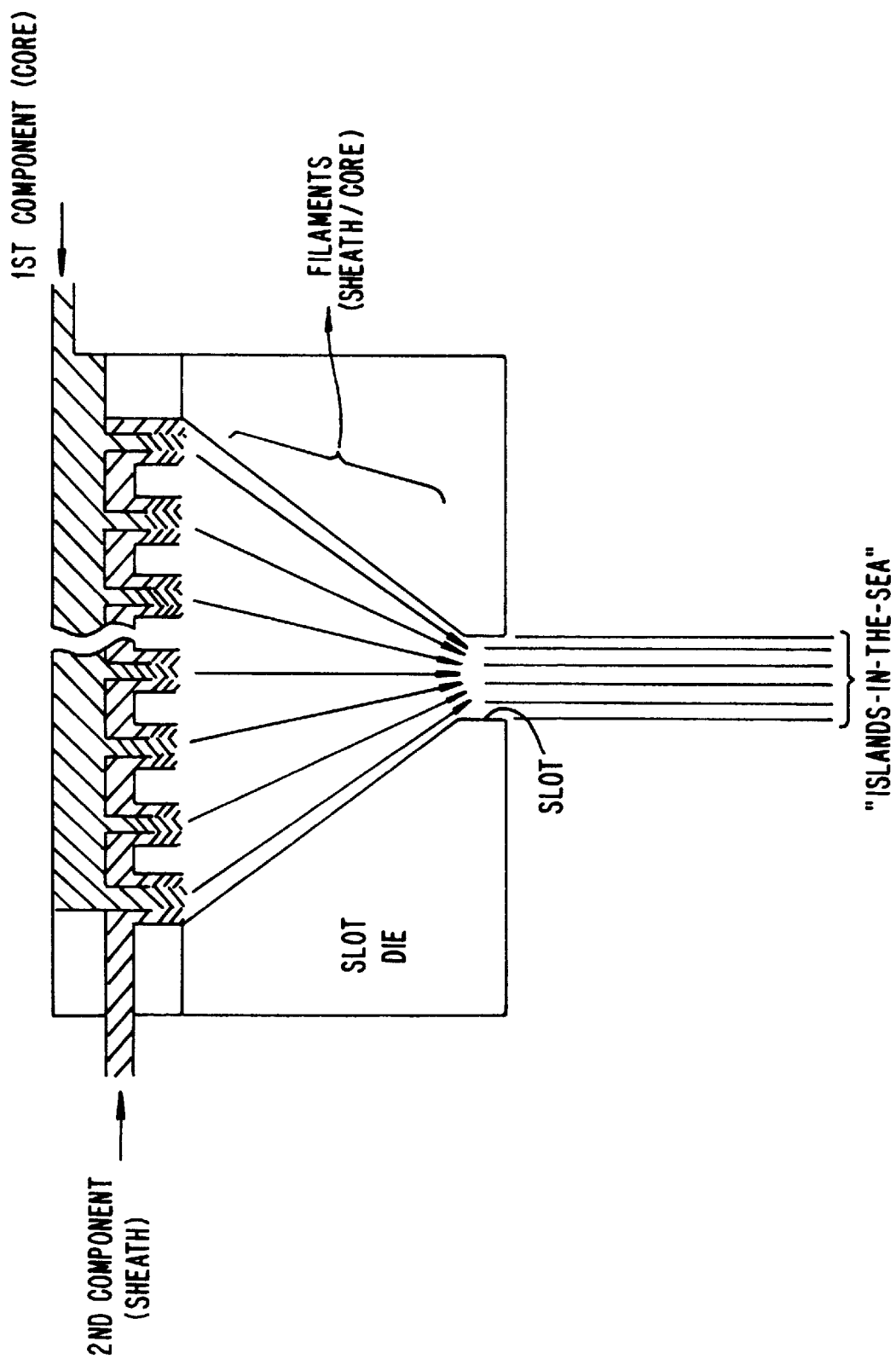
FIG. 2a shows the die-and-slot arrangement for producing the "islands-in-the-sea" embodiment.

A preferred method for forming a dental floss of the "islands-in-the-sea" embodiment of this invention is shown schematically in FIG. 1a. Again, two or more polymers are coextruded through a two-component coextrusion die, as described above. After the multiple multicomponent melt exits the plate, the strands are immediately drawn through another die having a single slot having the desired cross-section of the final floss, as shown in FIG. 2a. This step is performed before the polymer components quench. The melt strands are the cross-sectional area of the filaments, the filaments are forced together as they enter the slot and the molten sheath material of the core-and-sheath filaments coalesces around the individual core filaments to form the "sea."

Because the filaments are forced through the small slot to cause the sheath component to coalesce, pressure may build up between the spinneret and the slot die. Too much pressure will cause undesirable polymer leakage between the plates. Acceptable operating conditions without much leakage occur when a 34-filament, 0.7 mm-diameter hole spinneret is used to coextrude filaments which then pass through a 15×0.17 mm slot die, at a total flow rate of polymer of 40–60 grams/min. Resulting diameters of the core filaments in this embodiment may range from 0.001 to 0.010 inches, with a preferred range of 0.003 to 0.006 inches.

The polymer stream with embedded filaments leaving the slot die is quenched in a water bath before being processed as described above for the first embodiment. After drawing and windup, no further treatment (such as coating and twisting the floss) is necessary.

The first steps for manufacturing the embodiment of the "islands-in-the-sea" floss with an outer sheath surrounding the sea are the same as just described for the "islands-in-the-sea" embodiment. The outer sheath can be applied to the material exiting the slot portion of the die assembly in at least a couple of ways. First, dip-coating or spraying of the third material onto the floss may be used, as is known in the art. Second, the slot portion of the die assembly may be incorporated into a coextrusion die in which the third material is coextruded around the already coextruded material exiting the slot. This set-up permits the "islands-in-the-sea" and its coextruded outer sheath to exit the die assembly already formed. Further processing of this embodiment is as is described above.

EXAMPLES

The following examples are put forth so as to provide those of ordinary skill in the art with a complete disclosure and description of how to make the multifilament flosses and carry out the extrusion methodology of the invention, and are not intended to limit the scope of what the inventors regard as their invention. Efforts have been made to ensure accuracy with respect to numbers used (e.g., amounts, temperatures, etc.) but some experimental errors in deviation should be accounted for.

Equipment Set-Up

The following equipment set-up and manufacturing procedure, shown schematically in FIG. 1, was used in the first three examples.

Two 1.5 inch diameter extruders were connected to a two component coextrusion die. The two extruders included 30/1 L/D ratio general purpose screws. The two-component coextrusion included a metering plate, a distributing plate, etched plates, and a spinneret. After being coextruded through the coextrusion die, the coextrudate was processed with a downstream filament spinning set-up to produce filaments. The downstream set-up included a cooling chamber, finish applicator, tensioner, drawing godets, relaxing godet, and winder. The coextrudate was cooled at the cooling chamber, stretched and relaxed by drawing and relaxing godets, and collected on the take-up winder.

The apparatus as just described was also used for examples 4 and 5, except that a water bath instead of a cooling chamber was used to quench the floss, as depicted in FIG. 1a, and the multiple filaments leaving the spinneret were then passed through a 15×0.17 mm slot die to produce the "islands-in-the-sea" monofilament embodiment.

Using the equipment set-up and procedures described above, the following specialty bicomponent flosses were formed:

| Sample No.: | 1 | 2 |
| --- | --- | --- |
| Cross-section | Multiple sheath/core filaments | Multiple sheath/core filaments |
| Components | TPE (PEBAX 2533); Nylon (4.0 relative viscosity (RV)) | TPE (HYTREL 3078); Nylon (4.0 RV) |
| Ratio | 30/70 | 30/70 |
| Drawdown ratio | 3.5 | 3.4 |
| # of filaments | 144 | 144 |
| Total Denier | 580 | 732 |
| Tensile strength (g/denier) (gpd) | 5.0 | 4.1 |
| Break strength (kg) | 2.92 | 3.02 |
| Color / Additive | none | none |
| Comments | Fiber needs no bonding or twisting - can be used directly as floss by passing through heated draw rolls; non-bulking | non-bulking |

Figure 7:
FIG. 7 is an electronmicrograph of a filament containing kaolin particles in its sheath component.

| Sample No.: | 3 |
| --- | --- |
| Cross-section | Multiple sheath/core filaments |
| Components | Nylon (4.0 RV); Nylon (4.0 RV) |
| Ratio | 30/70 |
| Drawdown ratio | 3.0 |
| # of filaments | 144 |
| Total Denier | 622 |
| Tensile strength (g/denier) (gpd) | 3.4 |
| Break strength (kg) | 2.11 |
| Color / Additive | 2% kaolin in sheath |
| Comments | kaolin particles on surface observable in electron-micrograph (see FIG. 7) |

| Sample No.: | 4 | 5 |
| --- | --- | --- |
| Cross-section | Monofilament: single core filament in single sheath | Monofilament: multiple core filaments in single sheath |
| Components | Nylon (4.0 RV); TPE (PEBAX 2533) | Nylon (4.0 RV); TPE (HYTREL 3078) |
| Ratio | 70/30 | 70/30 |
| Drawdown ratio | 3.5 | 3.3 |
| # of filaments | Monofilament with single core filament | Monofilament with 34 embedded core filaments |
| Total Denier | 823 | 625 |
| Tensile strength (g/denier) | 3.6 | 4.5 |
| Break strength (kg.) | 3.9 | 2.8 |
| Color / Additive | none | none |
| Comments | Slot spinneret is 15 mm × 0.17 mm; monofilament is water-quenched | 34-hole die has hole diameter of 0.7 mm; slot spinneret is 15 mm × 0.17 mm; monofilament is water quenched |

| Sample No.: | 6 |
| --- | --- |
| Cross-section | Monofilament: Multiple core filaments in single sheath (islands-in-sea configuration) |
| Components | Nylon (4.0 RV) TPE (PEBAX 2533) |
| Ratio | 60/40 |
| Drawdown ratio | 3.5 |
| # of filaments | Monofilament with 34 embedded core filaments |
| Total Denier | 700 |
| Tensile strength (g/denier) | 3.7 |
| Break strength (kg.) | 2.6 |
| Color/Additive added to sheath | 6.0 wt. % pearlescent pigment (Hanna Color #10001295); 0.5 wt. % TiO$_2$ |
| Comments | 34-hole die has hole diameter of 0.7 mm; slot spinneret is 15 mm × 0.17 mm; monofilament is water quenched. Sample has a pearlescent appearance. |

Other embodiments are within the claims. For example, while bicomponent filaments have been described above in the Detailed Description, the filaments could contain any desired number of components, and in this case would be manufactured by extrusion through a suitable multicomponent die using the appropriate number of extruders.

The instant invention is shown and described herein in what is considered to be the most practical, and preferred embodiments. It is recognized, however, that departures may be made therefrom which are within the scope of the invention and that obvious modifications will occur to one skilled in the art upon reading this disclosure.

We claim:

1. A multicomponent, coextruded, monofilament dental floss comprising a core comprising a first material, embedded in a sheath comprising a second material and having a continuous outer surface.

2. The dental floss of claim 1 comprising a plurality of cores, each core comprising said first material, wherein each core is embedded in and substantially surrounded by said sheath.

3. The dental floss of claim 2 having a denier in the range of about 500 to about 1500.

4. The dental floss of claim 2 having a tensile strength from about 3 to about 5 grams per denier.

5. The dental floss of claim 1, wherein the outer surface of said floss has a coefficient of friction from about 0.09 to about 0.3.

6. The dental floss of claim 2 having an elongation at break in the approximate range of about 300% to about 1500%.

7. The dental floss of claim 2 wherein said sheath comprises an interior portion comprising said second material in which said cores are embedded, and an outer portion comprising a surface material, said outer portion providing said outer surface of said floss.

8. The dental floss of claim 1 wherein said first material of said core has a predetermined morphological structure, and said second material of said sheath has a different morphological structure.

9. The dental floss according to claim 1 wherein said second material imparts slipperiness to said continuous, outer surface.

10. A dental floss of claim 1 wherein said core has a multilobal radial cross-section.

11. The dental floss of claim 1 wherein said first material of said core is a melt-spinnable polymer selected to provide strength to the floss, and said second material of said sheath is selected to provide at least one predetermined physical characteristic to the floss.

12. The dental floss of claim 7 wherein said first material of said core is selected to provide strength to the floss, said each of said second and surface materials of said sheath is selected to provide at least one predetermined physical characteristic to the floss.

13. The dental floss of claim 11 wherein said first material comprises a polymer selected from the group consisting of nylon, polyester and polypropylene.

14. The dental floss of claim 11 wherein said second material comprises a melt-extrudable polymer selected from the group consisting of thermoplastic elastomers, ethylene vinyl acetate, ethylene propylene copolymers, fluoropolymers, lubricating polymers, and lubricous polymer blends and alloys.

15. The dental floss of claim 11 wherein said second material comprises a blend of a melt-extrudable polymer and a silicone oil and/or a mineral oil.

16. The dental floss of claim 11 wherein said second material comprises a blend of a melt-extrudable polymer and a particulate filler selected from the group consisting of kaolin, talc, calcium carbonate, silica, and polytetrafluoroethylene.

17. The dental floss according to claim 16 wherein an additive is absorbed into a surface of said particulate filler.

18. The dental floss of claim 16 wherein an additive is adsorbed onto a surface of said particulate filler.

19. The dental floss of claim 11 wherein one or more of the materials of the floss includes an additive.

20. The dental floss of claim 19 wherein the additive is selected from the group consisting of colors, pigments, fragrances, flavors, therapeutically-active ingredients, and agents which modify the interfacial adhesion between the materials of the floss.

21. The dental floss according to claim 20 wherein said additive comprises a pearlescent pigment.

22. The dental floss according to claim 21 wherein said pearlescent pigment is in said second material.

23. The dental floss according to claim 21 wherein said pearlescent pigment is in said first material.

24. The dental floss of claim 19 wherein the additive is incorporated into the floss in a manner to allow said additive to be released from the floss during use.

25. The dental floss of claim 19 wherein one or more of the materials of the floss is water-soluble, to allow the additive to leach from the floss during use.

26. A multicomponent, monofilament dental floss having an outer surface and at least one core embedded in a sheath providing said outer surface, made by a process comprising:

coextruding two or more materials through a multicomponent die assembly to form coextrudate comprising at least one core having a first material, said at least one core embedded in said sheath having a second material; and treating said coextrudate to form said dental floss.

27. A method of making a multicomponent, coextruded monofilament dental floss and at least one core embedded in a sheath, said method comprising:

coextruding two or more materials through a multicomponent die assembly to form coextrudate comprising said at least one core having a first material, said at least one core embedded in said sheath having a second material;

treating said coextrudate to form said dental floss.

28. The method of claim 27 wherein said materials comprise melt-extrudable polymers.

29. The method of claim 27 wherein the coextruding step comprises:

forming multicomponent filaments having cores of said first material and sheaths of said second material; and causing the second material of each multicomponent filament sheath to combine to form said sheath in which said core filaments are embedded, the resulting molten coextrudate leaving the die assembly with the core filaments embedded in said sheath.

30. The method of claim 27 wherein the die assembly comprises an integral unit.

31. The method of claim 27 wherein the die assembly comprises an upper die for extruding said at least one filament, and a lower die for embedding said at least one filament in said sheath.

32. The method of claim 31 wherein said upper die comprises a spinneret having a predetermined number of apertures.

33. The method of claim 27 wherein said at least one core comprises a melt-extrudable polymer selected to provide strength to the floss, and said sheath comprises a second component selected to provide at least one predetermined physical characteristic for the floss.

34. The method of claim 27 comprising incorporating an additive into one or more of the materials before or during coextrusion.

35. The method of claim 34 wherein the additive is selected from the group consisting of colors, pigments, fragrances, flavors and therapeutically-active ingredients.

36. The method of claim 34 wherein the additive is incorporated in a manner to allow said additive to be released from the floss during use.

37. The method of claim 27 wherein the coextruding step comprises:

forming a plurality of multicomponent filaments having cores of said first material and sheaths of said second material;

forming an intermediate coextrudate comprising causing the second material of each multicomponent filament sheath to combine to form a body sheath in which said cores are embedded; and coextruding said intermediate coextrudate with a surface material to form an outer sheath portion of said sheath, the resulting molten coextrudate leaving the die assembly with the cores embedded in said body sheath and said body sheath surrounded by said outer sheath portion.

38. The method of claim 27 where the treating step comprises quenching the molten coextrudate and drawing the floss.

39. A method of flossing teeth, comprising:

inserting between two teeth a length of multicomponent, monofilament, coextruded dental floss comprising at least one core embedded in a sheath.

* * * * *